United States Patent [19]

Arnone et al.

[11] Patent Number: 4,661,907

[45] Date of Patent: Apr. 28, 1987

[54] METHOD FOR DETERMINING AN ANGSTROM EXPONENT FOR CORRECTING SATELLITE COLOR SCANNER IMAGES

[75] Inventors: Robert A. Arnone; Ronald J. Holyer, both of Carriere, Miss.

[73] Assignee: The United States of America as represented by the Secretary of the Navy, Washington, D.C.

[21] Appl. No.: 778,827

[22] Filed: Sep. 23, 1985

[51] Int. Cl.$^4$ .......................... G06F 15/20; G01J 5/00
[52] U.S. Cl. ..................... 364/420; 364/518; 364/526; 358/109; 374/124; 354/65
[58] Field of Search ............... 364/400, 420, 514–518, 364/521–522, 525–526; 382/16–19; 358/95, 109, 113, 902; 356/300, 302–303, 307, 319–320; 342/351–352; 374/100–101, 121, 124, 137; 354/65, 67, 76, 100, 354; 250/330, 334, 338, 340

[56] References Cited

U.S. PATENT DOCUMENTS

| | | | |
|---|---|---|---|
| 2,430,277 | 11/1947 | Cooke | 35/41 |
| 3,242,836 | 3/1966 | Bartsch | 354/65 X |
| 3,676,581 | 7/1972 | Swet | 358/109 X |
| 3,752,914 | 8/1973 | England et al. | 358/109 X |
| 4,143,400 | 3/1979 | Heckman, Jr. et al. | 358/95 |
| 4,227,211 | 10/1980 | Disbrow | 382/17 X |
| 4,293,945 | 10/1981 | Atia et al. | 370/17 |
| 4,364,085 | 12/1982 | Dalke | 358/109 X |
| 4,463,357 | 7/1984 | MacDoran | 343/460 |
| 4,469,443 | 9/1984 | Geller | 356/364 |
| 4,483,614 | 11/1984 | Rogers | 356/28.5 |
| 4,499,470 | 2/1985 | Stacey | 343/352 |
| 4,611,929 | 9/1986 | Holyer | 374/124 |

*Primary Examiner*—Gary V. Harkcom
*Attorney, Agent, or Firm*—Thomas M. Phillips

[57] ABSTRACT

Effective removal of atmospheric contamination for a sequence of satellite color scanner ocean imagery is achieved through determination of an optimum Angstrom exponent for weighting data in a plurality of channels of different wavelengths by the method of providing a refresh plane display for data from one channel, weighting data from a selected reference channel as determined by an Angstrom exponent, interacting the weighted reference channel data with the data in the plane by subtraction therefrom to reveal atmospheric aersol bands, varying the Angstrom exponent to determine an optimum value at which the aerosol bands become transparent, and then weighting data from each of the channels by use of that optimum value.

4 Claims, 2 Drawing Figures

METHOD FOR DETERMINING AN ANGSTROM EXPONENT FOR CORRECTING SATELLITE COLOR SCANNER IMAGES

BACKGROUND OF THE INVENTION

This invention relates to the field of satellite collection of geophysical data, and more particularly to an improved method of processing ocean color data collected over a plurality of color channels by a satellite carried CZCS (Coastal Zone Color Scanner) so as to remove atmospheric contamination errors from the data.

One major promise of ocean color satellite data has been the possibility of quantitatively relating these data to bichemical ocean processes and ocean circulation.

A major problem with obtaining absolute ocean color measurements and imagery from a spaceborne sensor is caused by the intervening atmosphere. Ninety percent of the signal received by the satellite sensor is of atmospheric origin. Atmospheric removal algorithms have been developed that have had encouraging results. However, calculating the radiance attributed to aerosol scattering can have problems that are a result of incorrectly estimating the aerosol characteristics. It is desirable, therefore, to provide an improved method for eliminating atmospheric contamination in CZCS imagery by selecting the optimum aerosol characteristics that can be applied to the entire image.

It has been shown for continental air masses that aerosol optical thickness $T_A$ and single scattering albedo $\omega_A$ can be assumed to be a continuous function strongly dependent on wavelength and that the ratio of the aerosol optical thickness at specific wavelengths is related to a power law. Thus the approximation, $$\left(\frac{\lambda_o}{\lambda}\right)^\eta = \frac{\omega_A^\lambda T_A^\lambda \rho(\theta,\theta,\lambda)}{\omega_A^{\lambda_o} T_A^{\lambda_o} \rho(\theta,\theta_o,\lambda_o)} \quad \text{[Eq. 1]}$$

where

- $\eta$ is termed the Angstrom exponent
- $\omega_A$ = single scattering albedo of aerosols
- $Y_A$ = aerosol optical thickness
- $\Theta$ = zenith angle from satellite
- $\Theta_o$ = solar zenith angle
- $\lambda_o$ = reference wavelength
- $\lambda$ = wavelength of interest
- $\rho = (\Theta,\Theta_o,\lambda)$ scattering phase function Atmospheric transmittance $\tau$ as a function of wavelength $\lambda$ may then be expressed as $$\tau(\lambda) = (\lambda/\lambda_o)^\eta \quad \text{[Eq. 2]}$$

SUMMARY OF THE INVENTION

The solution to obtaining the water-leaving radiance at the sea surface can be summarized as eliminating the atmospheric signal through a weighted subtraction of the radiation received at the reference channel from each of a plurality of adjacent visible channels. The major uncertainty in this technique is selecting the optimum Angstrom coefficient exponent to be used in calculating the weight.

With the foregoing in mind, it is a principal object of this invention to provide an Angstrom coefficient (exponent) determining method for use in processing multiple channels of color data to remove atmospheric contamination errors so as to affect substantially accurate color imagery across a plurality of CZCS channels.

Another important object is the provision of an interactive data processing method of the foregoing character that is relatively simple to carry out utilizing existing apparatus.

Still another object is the provision of an Angstrom exponent selection technique that is independent of a "clear" ocean area determination.

Other objects, advantages and novel features of the invention will become apparent from the following detailed description of the invention when considered in conjunction with the accompanying drawings.

DESCRIPTION OF THE PREFERRED EMBODIMENT

Figure 1:
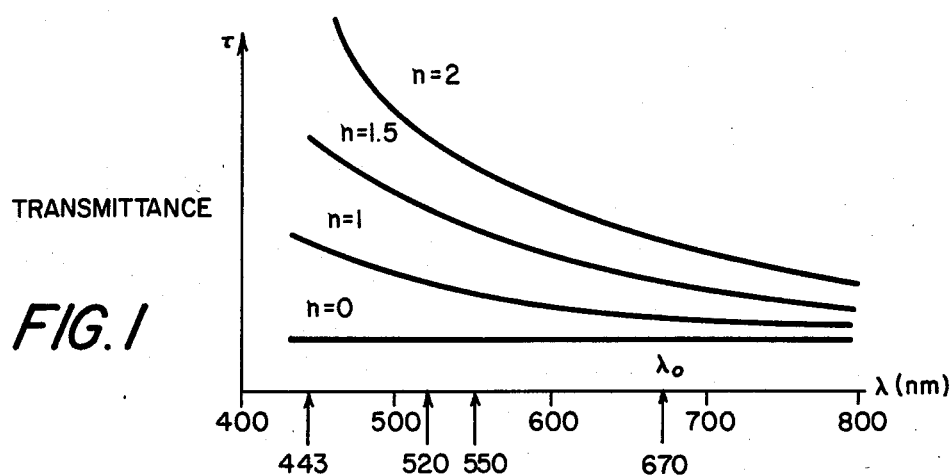
FIG. 1 is a graphic illustration of a family of curves illustrating Angstrom exponents corresponding to transmittance vs wavelength.

Referring first to FIG. 1 and recalling Eq. 2, it will be noted the atmospheric transmittance $\tau$ as a function of wavelength can be represented as a family of curves corresponding to different Angstrom exponents. In the present example the channel centered on 670 nm is taken as the $\lambda_o$ reference channel. Thus, were the atmospheric transmittance the same for wavelengths of all of the channels, an Angstrom exponent $\eta$ of 0 (zero) would be required to make $(\lambda/670)^\eta =$ unity, and this equal transmittance condition is represented by the horizontal curve $\eta=0$ in FIG. 1. In actual practice the transmittance varies across the channels and a family of curves for different values of $\eta$ would exist, as shown representing at $\eta=1$, $\eta=1.5$, and $\eta=2$.

Figure 2:
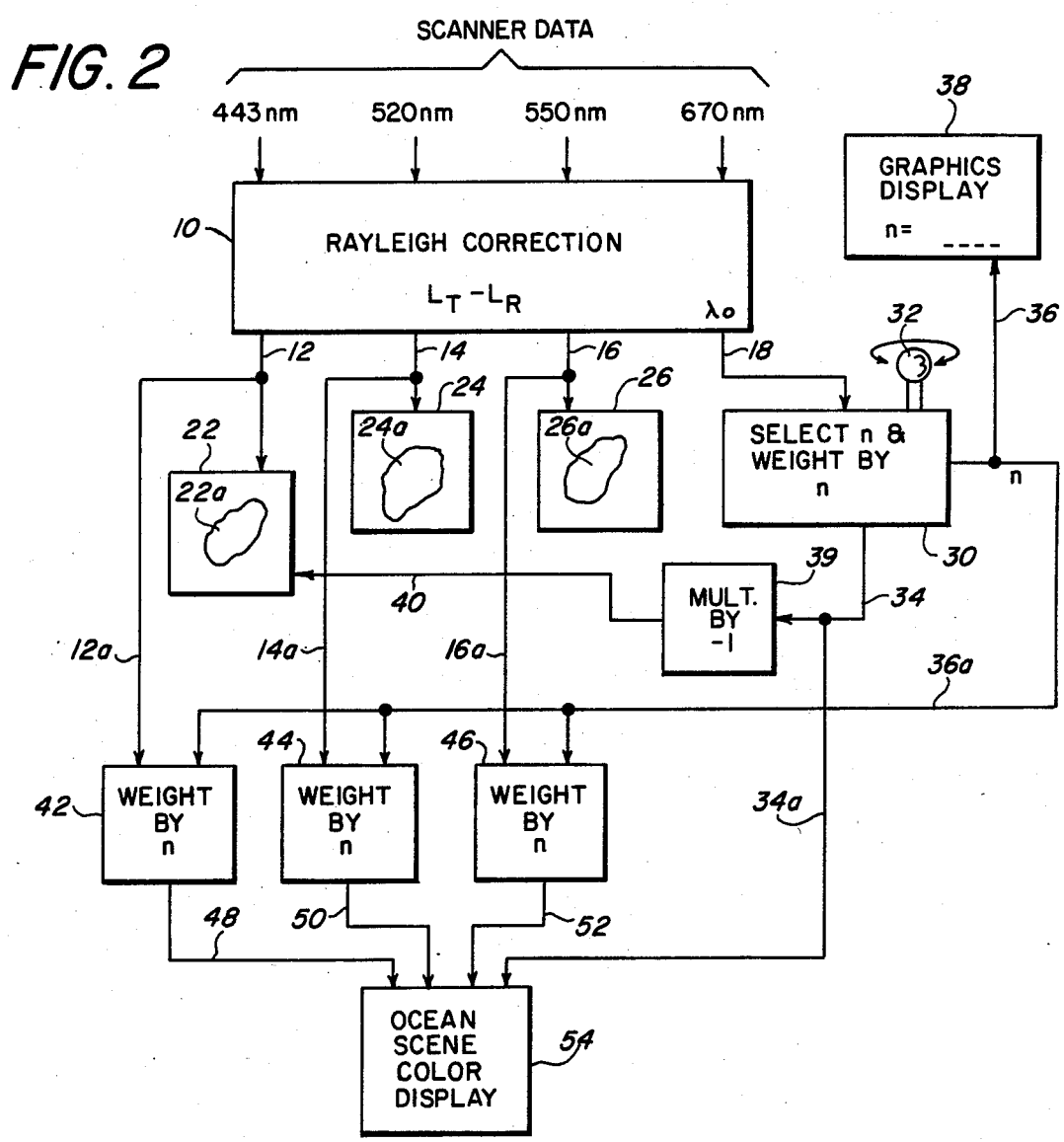
FIG. 2 is a diagrammatic illustration of the technique of the invention.

Referring now to FIG. 2, the Rayleigh correction $(L_T - L_R)$ of the data for each of the three visible channels and the reference channel is represented by block 10, with the resulting Rayleigh corrected data being shown by flow lines 12, 14, 16 and 18. The Rayleigh corrected data for at least one of the visible channels, e.g., the 433 nm channel, line 12, is applied as a first input for display on a refresh plane 22. In the embodiment being described, the refresh plane 22 is a 512×512 CRT having 8-bit resolution and provides a visible image 22a of a predetermined area of ocean scene viewed by the CZCS. Full resolution (0.8 km) CACS imagery can be displayed representing an area of approximately 400 km on a side. For a reason which will later be made apparent, display 22 may be referred to as the interactive display. While not necessary to carrying out the invention, the Rayleigh corrected data 14 and 16 of the other visible channels can be similarly applied to refresh planes 24 and 26 to display images 24a and 26a.

The Rayleigh corrected output 18 of the 670 nm $\lambda_o$ reference channel is weighted as shown at block 30 by a selected intermediate value of Angstrom exponent $\eta$, within a range of say −1 to +3, the weight being computed as:

$$\text{weight} = \left[\frac{F_o^\lambda e^{(-2 \cdot T_{oz}^\lambda)}}{F_o^{670} e^{(-2 \cdot T_{oz}^{670})}}\right] \left(\frac{670}{\lambda}\right)^\eta \quad [\text{Eq. 3}]$$

where $F_o$ = extraterrestrial solar radiance above the atmosphere, $T_{oz}$ = ozone optical thickness, and $\lambda$ = the wavelength of the channel being weighted.

The selected Angstrom exponent $\eta$ can be continuously varied by manual rotation of a trackball 32 to correspondingly vary the weighting of the weighted reference data represented by flow line 34. The value of $\eta$ is applied via line 36 to a graphics display 38 so as to be visually presented to an operator, and changes with rotation of the trackball.

The weighted reference data 34 is rendered negative at 39 and applied as shown at 40 as a second input to the interactive refresh plane 22. In that plane, the data interacts such as to subtract the weighted reference data (weighted by $\eta$) from the 443 nm channel data 12 and the difference is displayed as image 22a.

Now, variation of the Angstrom exponent $\eta$ by rotation of the trackball produces a real-time change in the differential display at the interactive display 12. Rotation of the trackball by the investigator results in the interactive display 22 changing from oversubtraction ($\eta = +3$) of the 670 nm channel to undersubtraction ($\eta = -1$). The aerosol patterns within the display correspondingly change from dark to light. At some intermediate Angstrom exponent value of $\eta$, the aerosol patterns become transparent, and ocean color features are displayed at 22. The value of $\eta$ may then be considered as optimum for the entire image.

That value of $\eta$ is then used to weight each the channels according to Eq. 3. Thus, Rayleigh corrected data, lines 12a, 14a, and 16a is weighted by $\eta$ (line 36a) as represented by blocks 42, 44, 46, respectively to provide appropriately weighted data, lines 48, 50, and 52, which can be combined with one another and with the weighted reference data, line 34a for any additional conventional processing and accurate ocean color imaging at display 54.

Obviously many modifications and variations of the present invention are possible in light of the above teachings. It is therefore to be understood that within the scope of the appended claims the invention may be practiced otherwise than as specifically described.

What is claimed is:

1. A method for determining an optimum Angstrom coefficient $\eta$ for use in weighting satellite scanner collected ocean image data in a plurality of different visible wavelength data channels, said method comprising the steps of:

effecting Rayleigh correction of said data by subtracting Rayleigh contribution from total radiance in each of said channels to provide Rayleigh corrected data in each;

applying said Rayleigh corrected data of at least one of said channels to an interactive display as a refresh plane;

selecting another of said channels as a reference data channel;

weighting the reference channel Rayleigh corrected data by an intermediate value of $\eta$ in a weighting function with $\eta$ being in the range of about $\eta = -1$ to about $+3$ to provide weighted reference channel data;

applying said weighted reference channel data as a negative input to said interactive display so as to subtract said weighted reference data from the refresh plane to display aerosol bands in said refresh plane; and varying the intermediate value of $\eta$ within said range until said aerosol bands become transparent at an optimum value of $\eta$; and weighting said Rayleigh corrected data of said one of said channels by said optimum value of $\eta$.

2. The method defined in claim 1, and wherein:
said weighting function is $$\text{weight} = \frac{F_o^\lambda e^{(-2 \cdot T_{oz}^\lambda)}}{F_o^{\lambda_o} e^{(-2 \cdot T_{oz}^{\lambda_o})}} \left(\frac{\lambda_o}{\lambda}\right)^\eta$$

where $F_o$ = extraterrestrial solar radiance above the atmosphere, $Y_{oz}$ = ozone optical thickness, $\lambda_o$ = wavelength of said reference channel, and $\lambda$ = wavelength of said at least one of said channel.

3. The method defined in claim 2, and further comprising the step of:

weighting said Rayleigh corrected data of the others of said channels by said optimum value of $\eta$; and combining the weighted data of each of said channels in an ocean image color display.

4. The method of claim 3, and wherein said weighting of said data for each of said channels is effected simultaneously by said optimum value of $\eta$; and said optimum value of $\eta$ is selected by operator manipulation of a control while observing of said refresh plane on said interactive display.

* * * * *